US010932976B2

(12) United States Patent
Conner et al.

(10) Patent No.: US 10,932,976 B2
(45) Date of Patent: *Mar. 2, 2021

(54) LEFT RADIAL ACCESS, RIGHT ROOM OPERATION, PERIPHERAL INTERVENTION SYSTEM

(71) Applicant: TRANS-RADIAL SOLUTIONS LLC, Roebuck, SC (US)

(72) Inventors: James E. Conner, Landrum, SC (US); Barney C. Wasson, Jr., Grey Court, SC (US); Andrew W. Shealy, Roebuck, SC (US)

(73) Assignee: TRANS-RADIAL SOLUTIONS LLC, Roebuck, SC (US)

( * ) Notice: Subject to any disclaimer, the term of this patent is extended or adjusted under 35 U.S.C. 154(b) by 203 days.

This patent is subject to a terminal disclaimer.

(21) Appl. No.: 16/239,943

(22) Filed: Jan. 4, 2019

(65) Prior Publication Data

US 2019/0167501 A1    Jun. 6, 2019

Related U.S. Application Data

(63) Continuation of application No. 14/780,714, filed as application No. PCT/US2014/034788 on Apr. 21, 2014, now Pat. No. 10,548,795.

(60) Provisional application No. 61/856,754, filed on Jul. 21, 2013.

(51) Int. Cl.
| *A61G 13/12* | (2006.01) |
| *A61G 7/05* | (2006.01) |
| *A61B 6/04* | (2006.01) |
| *A61B 6/10* | (2006.01) |
| *G21F 1/00* | (2006.01) |
| *A61B 6/12* | (2006.01) |

(52) U.S. Cl.
CPC ........ *A61G 13/1235* (2013.01); *A61B 6/0407* (2013.01); *A61B 6/107* (2013.01); *A61B 6/12* (2013.01); *A61G 7/0513* (2016.11); *G21F 1/00* (2013.01); *A61G 2210/50* (2013.01)

(58) Field of Classification Search
CPC ............... A61G 13/122; A61G 13/123; A61G 13/1235; A61G 7/0513; A61G 2210/50; A61B 6/0407; A61B 6/107; A61B 6/12; G21F 1/00
See application file for complete search history.

(56) References Cited

U.S. PATENT DOCUMENTS

| 4,662,366 A | * | 5/1987 | Tari | ........................ | A61F 5/3723 128/877 |
| 5,006,718 A | * | 4/1991 | Lenhart | .................. | A61B 6/107 250/515.1 |
| 7,103,932 B1 | * | 9/2006 | Kandora | .............. | A61B 6/0407 5/613 |

(Continued)

FOREIGN PATENT DOCUMENTS

WO    2013089608 A1    6/2013

*Primary Examiner* — David R Hare
(74) *Attorney, Agent, or Firm* — Thrive IP; Bernard Klosowski

(57) ABSTRACT

Systems and methods for left radial access, right room operation peripheral interventions are provided that include left radial bases to stabilize a left arm of a cardiac patient across a midsagittal plane, transradiant right radial bases to position a right arm of the patient, and radiodense radiation reduction barriers located between the patient and a doctor.

23 Claims, 10 Drawing Sheets

(56) References Cited

U.S. PATENT DOCUMENTS

| | | | | |
|---|---|---|---|---|
| 8,369,933 | B2* | 2/2013 | Crisco | A61G 13/1235 |
| | | | | 600/424 |
| 8,700,131 | B2* | 4/2014 | Goff | A61B 6/107 |
| | | | | 600/424 |
| 10,548,795 | B2* | 2/2020 | Conner | A61B 6/0407 |
| 2007/0011814 | A1* | 1/2007 | Rotert | A61G 13/12 |
| | | | | 5/646 |
| 2007/0029513 | A1* | 2/2007 | Treuth | A61B 6/107 |
| | | | | 250/519.1 |
| 2011/0184278 | A1 | 7/2011 | Goff et al. | |
| 2012/0241652 | A1* | 9/2012 | Jeschke | A61B 6/107 |
| | | | | 250/519.1 |
| 2013/0320246 | A1* | 12/2013 | Beck | A61M 25/00 |
| | | | | 250/515.1 |
| 2014/0029720 | A1* | 1/2014 | Osherov | A61B 6/4441 |
| | | | | 378/62 |
| 2015/0351707 | A1* | 12/2015 | Sampognaro | A61B 6/0428 |
| | | | | 600/436 |

\* cited by examiner

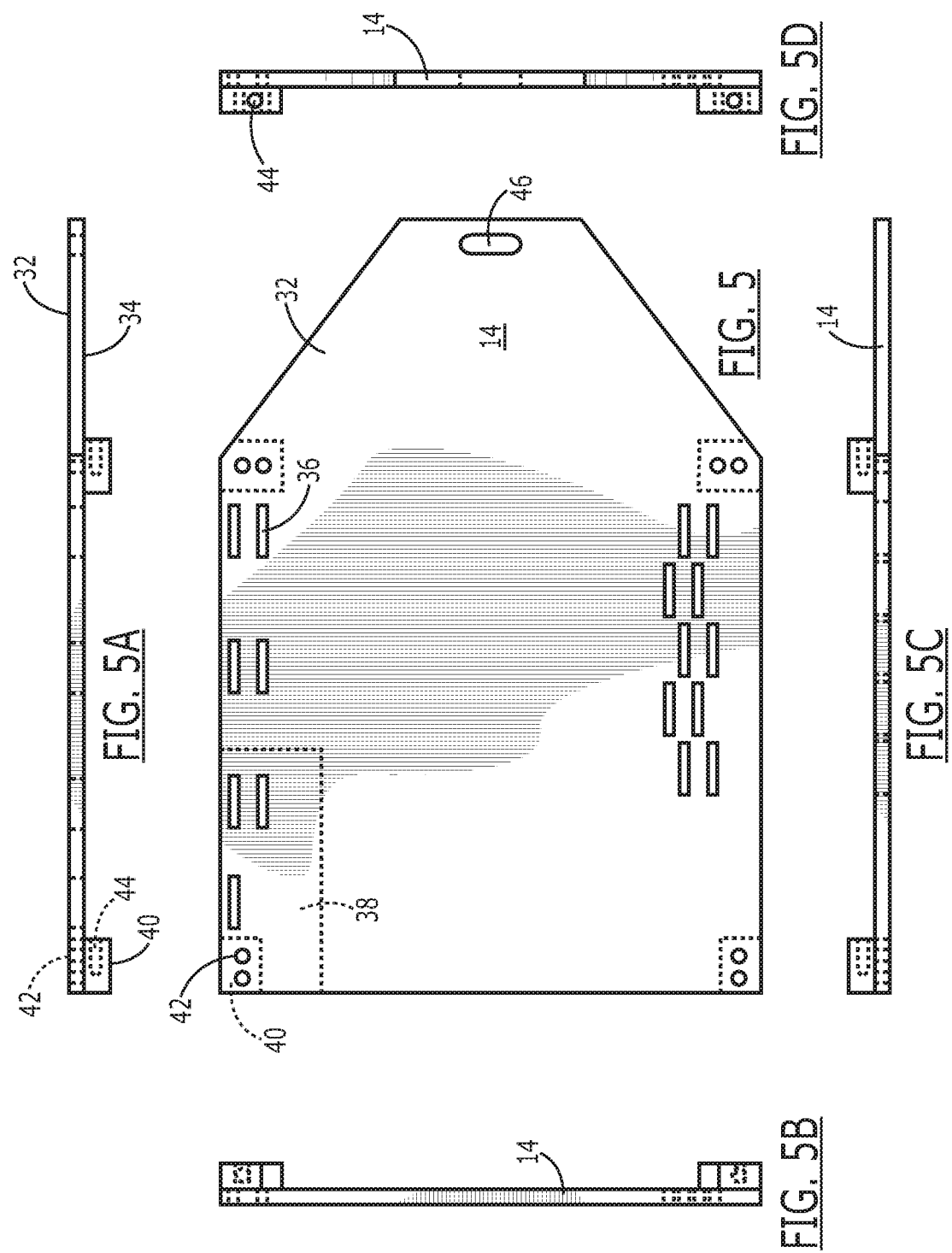

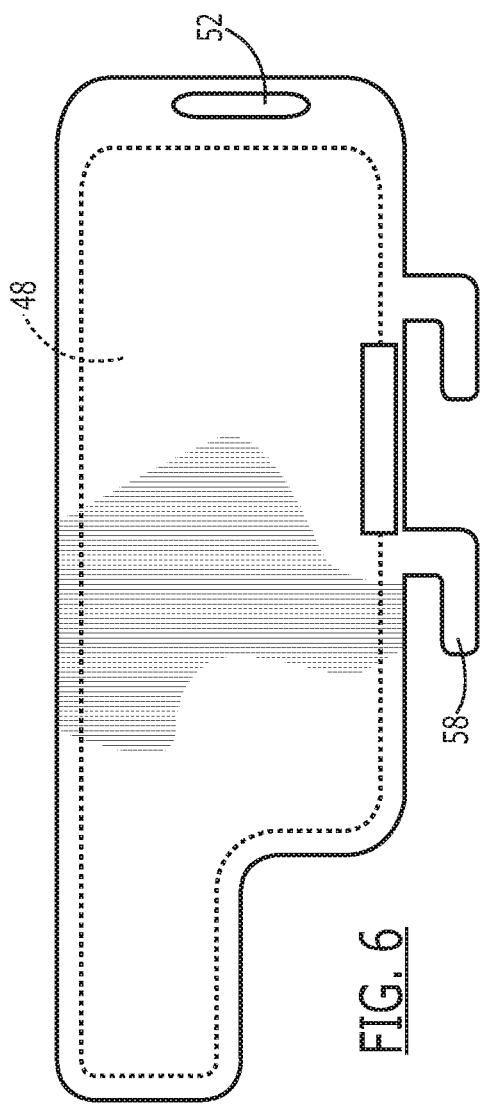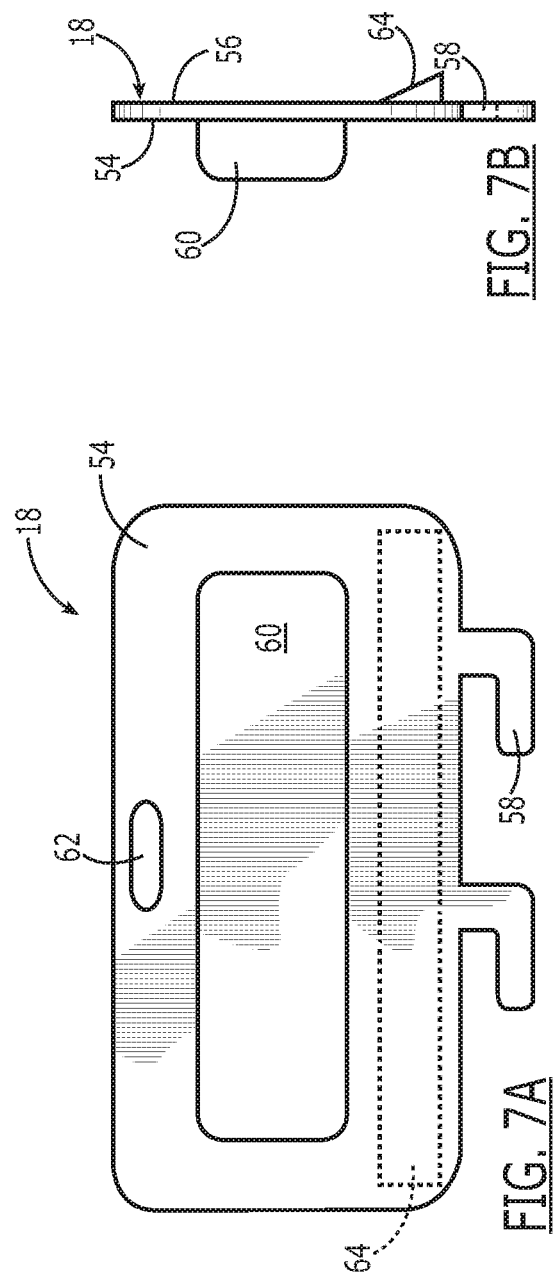

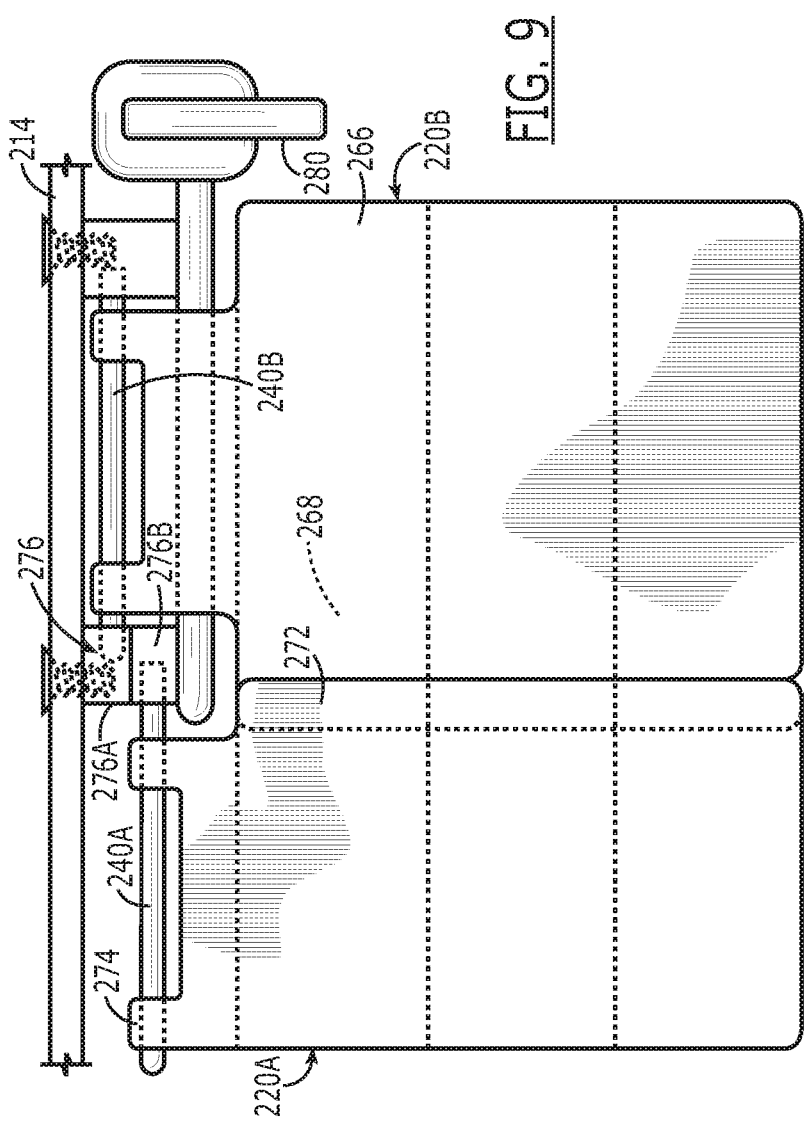
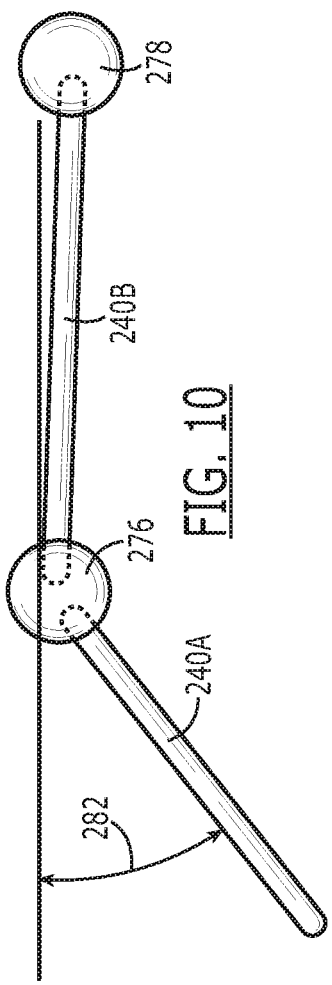

| Standard Shielding | | | | | Cardiologist | Techniques | |
|---|---|---|---|---|---|---|---|
| Position 1=Eyes | Position 2=Chest | Position 3=Waist | Position 4=Knees | | | EVP | 60 |
| 100 mR/hr | 95 mR/hr | 50 mR/hr | 50 mR/hr | A/P (0.0) | | mA | 40 |
| 100 mR/hr | 118 mR/hr | 54 mR/hr | 11.4 mR/hr | RAO 36 CRA 21 | | Exposure Time | 5 Seconds |
| 96 mR/hr | 153 mR/hr | 110 mR/hr | 3.8 mR/hr | LAO 33 CRA 21 | | FOV | 20 cm |
| 97.2 mR/hr | 168 mR/hr | 70.1 mR/hr | 17.8 mR/hr | LAO 31 CAU 30 | | Table Height | 36 in |
| 13.5 mR/hr | 4.4 mR/hr | 32 mR/hr | 4.8 mR/hr | RAO 28 CAU 0 | | S/O | 100 cm |
| 81.7 mR/hr | 107.7 mR/hr | 63.2 mR/hr | 17.6 mR/hr | Average mR/hr | | Phantom | 21 cm Water |
| Added Shielding | | | | | Cardiologist | Distance from center of Phantom to Cardiologist | 25 in |
| 29 mR/hr | 22 mR/hr | 16.2 mR/hr | 3.8 mR/hr | A/P (0.0) | | | |
| 101 mR/hr | 35 mR/hr | 16.3 mR/hr | 7.3 mR/hr | RAO 36 CRA 21 | | Distance from center of Phantom to Technologist | 44 in |
| 46 mR/hr | 21 mR/hr | 12.3 mR/hr | 2.9 mR/hr | LAO 22 CRA 21 | | | |
| 45 mR/hr | 61 mR/hr | 21.2 mR/hr | 8.7 mR/hr | LAO 31 CAU 30 | | Meters Used | Inovison 451-P Victoreen 451-P RYR |
| 28 mR/hr | 13.2 mR/hr | 7.9 mR/hr | 3.4 mR/hr | RAO 28 CAU 0 | | Mode | Exposure Rate |
| 49.8 mR/hr | 30.4 mR/hr | 14.7 mR/hr | 5.2 mR/hr | Average mR/hr | | | |
| 39% | 71.70% | 76.70% | 70.45% | Cardiologist Reduction | | 64.4% Average | |

| Fig. 11A |
|---|
| Fig. 11B |

FIG. 11B (continued from Fig. 11A)

| | | | | Cardiologist | |
|---|---|---|---|---|---|
| Standard Shielding | | | | | |
| 28 mR/hr | 30 mR/hr | 16 mR/hr | 27 mR/hr | A/P (0.0) | |
| 70 mR/hr | 63 mR/hr | 15 mR/hr | 14.1 mR/hr | RAO 36 CRA 21 | |
| 75 mR/hr | 70 mR/hr | 14.2 mR/hr | 18.4 mR/hr | LAO 33 CRA 21 | |
| 42.5 mR/hr | 45 mR/hr | 13.1 mR/hr | 15.9 mR/hr | LAO 31 CAU 30 | |
| 29 mR/hr | 27 mR/hr | 7 mR/hr | 5.7 mR/hr | RAO 28 CAU 0 | |
| 49.8 mR/hr | 47 mR/hr | 13.1 mR/hr | 16.2 mR/hr | Average mR/hr | |
| Added Shielding | | | | | |
| 17.5 mR/hr | 5.9 mR/hr | 3.6 mR/hr | 3.4 mR/hr | A/P (0.0) | |
| 85 mR/hr | 17.7 mR/hr | 10.3 mR/hr | 8.4 mR/hr | RAO 36 CRA 21 | |
| 36 mR/hr | 11.4 mR/hr | 6.3 mR/hr | 9.8 mR/hr | LAO 22 CRA 21 | |
| 22 mR/hr | 9.8 mR/hr | 6.7 mR/hr | 4.5 mR/hr | LAO 31 CAU 30 | |
| 30 mR/hr | 11.8 mR/hr | 11.8 mR/hr | 2.7 mR/hr | RAO 28 CAU 0 | |
| 38.1 mR/hr | 11.1 mR/hr | 7.7 mR/hr | 5.8 mR/hr | Average mR/hr | |
| 22% | 75.7% | 40.9% | 64.8% | Technologist Reduction | 50.8% Average |

FIG. 11B

LEFT RADIAL ACCESS, RIGHT ROOM OPERATION, PERIPHERAL INTERVENTION SYSTEM

CROSS-REFERENCE TO RELATED APPLICATIONS

This utility patent application is a continuation of, and claims priority to, U.S. patent application Ser. No. 14/780,714, filed in the United States Patent and Trademark Office on Sep. 28, 2015, which claims priority to international patent application serial number PCT/US14/34788 filed in the United States Patent and Trademark Office as the Receiving Office on Apr. 21, 2014, which claims benefit of U.S. Provisional Patent Application Ser. No. 61/856,754, filed in the United States Patent and Trademark Office on Jul. 21, 2013, all of which are incorporated herein by reference in their entireties.

BACKGROUND

Trans-radial access ("TRA") is an increasingly utilized procedure for peripheral interventions on catheter tables. Peripheral interventions via a patient's left wrist are advantageous from an anatomical standpoint. First, due to proximity and catheter support, sub-clavian, vertebral and certain carotid interventions are more easily performed via a patient's arm rather than the groin. Second, renal and mesenteric vessels have a superior oriented origin, and their access from the arm is easier and more natural. Third, lower extremity interventions, particularly iliac and proximal superficial femoral artery, are more accessible from the arm when there is contralateral disease, or if the iliac bifurcation is hostile.

For the treatment of iliac disease, there are specific potential advantages for a radial puncture compared with the more traditional femoral approach. Femoral access may be difficult when crossing an iliac lesion from the contralateral side. Moreover, precise stent placement may be problematic if contralateral iliac disease needs to be treated. In such cases, TRA may permit same-day discharge and prevent the need to access the contralateral groin and for crossover.

However, traditional TRA platforms do not permit both right and left radial access from either the left or right side of the table. Specifically, existing platforms do not permit left radial access and operation from the right side of the operating table. Additionally, existing arm boards that include radiolucent materials so as to not interfere with medical imaging provide little to no protection from ionizing radiation to, e.g., a doctor performing left radial access procedures from the right side of the catheter table.

What is needed in the field of trans-radial access is a left radial access, right room operation system that is also suitable for use during left radial lower extremity procedures. The system should also reduce or eliminate staff exposure to ionizing radiation during catheterization procedures without impairing the ability to obtain the necessary diagnostic medical images during the procedures. The system also should be economical to manufacture, and it should be simple, effective, and reliable to use and reuse.

BRIEF SUMMARY OF THE DISCLOSURE

The present disclosure is directed in general to left radial access, right room operation, lower extremity peripheral platforms for use in left radial peripheral interventions. More specifically, the trans-radial access platform provides radiation reduction and allows for left and right radial access, for different procedures, from lower extremity peripheral to pacemaker and cardiac interventions. As will be understood from the present disclosure and by its practice, the various embodiments described herein, and their equivalents are simple to manufacture, install and use.

For example, in one embodiment according to the present disclosure, a system is provided for use in supporting a patient lying in supine position with left arm secured across the patient's midsagittal or median plane during a lower extremity peripheral procedure. The system may be a left radial access, right room operation, peripheral intervention system for use with an imaging system. The peripheral intervention system may have a left radial base that stabilizes a left arm of a patient across a midsagittal plane of the patient during a lower extremity peripheral intervention on a procedure table. A right radial base may be positioned substantially parallel to an operating surface of the procedure table, the right radial base being transradiant and configured to position a right arm of the patient in a direction away from the midsagittal plane during the lower extremity peripheral intervention. Also, a radiation reduction barrier may be placed apart from the left radial base and from the right radial base, the radiation reduction barrier having a radiodense material disposed between the patient and an attending staff member to reduce scatter radiation from the patient in a direction of the staff member during a procedure.

In another embodiment, a left radial access, right room operation peripheral intervention system for use with an imaging system may include a base board being configured for connection proximate a table having a left side and a right side corresponding to a left arm and a right arm of a patient; a left radial base attached to the base board and being configured to cushion and stabilize a left arm of a cardiac patient across a midsagittal plane of the patient during a lower extremity peripheral intervention on the table, wherein an attending cardiologist may perform the intervention from the right side of the table; and a radiation reduction barrier spaced apart from the left radial base, the radiation reduction barrier having a radiodense material disposed between the patient and an attending staff member to reduce radiation scattering from the patient in a direction of the staff member.

In yet another embodiment, a left radial access, right room operation peripheral intervention system for use with an imaging system may have a base board being configured for attachment proximate a procedure table; a left radial base attachable to the base board and being configured to stabilize a left arm of a patient across a midsagittal plane of the patient during a lower extremity peripheral intervention on the procedure table; a right radial base attachable to the base board and disposed substantially parallel to an operating surface of the procedure table, the right radial base being transradiant and configured to position a right arm of the patient in a direction away from the midsagittal plane during the lower extremity peripheral intervention; a radiation reduction barrier attachable to the base board and spaced apart from the left radial base and from the right radial base, the radiation reduction barrier having a radiodense material disposed between the patient and an attending staff member to reduce radiation scattering from the patient in a direction of the staff member during an imaging procedure; and a radiodense apron releasably connected to the base board.

In a further embodiment, a left radial access, right room operation peripheral intervention system for use with an imaging system may include a right radial base having a base board attachable to a procedure table with a right side and a left side corresponding to a right arm and a left arm of a patient, the right radial base being disposed substantially parallel to an operating surface of the operating table, the right radial base board being disposed under the operating surface, the right radial base being transradiant and configured to position the right arm of the patient in a direction away from the midsagittal plane during the lower extremity peripheral intervention; a left radial base in connection with the right radial base board and being configured to stabilize a left arm of a patient across a midsagittal plane of the patient during a lower extremity peripheral intervention on the procedure table; a radiation reduction barrier attachable to a right radial base board under the table surface, the radiation reduction barrier spaced apart from the left radial base and from the right radial base, the radiation reduction barrier having a radiodense material disposed between the patient and an attending staff member to reduce radiation scattering from the patient in a direction of the staff member during an imaging procedure; and a radiodense apron releasably connected to the base board.

An exemplary method for left radial access and right room operation peripheral intervention system may include joining a left radial base proximate a procedure table having a left side corresponding to a left arm of a patient and a right side corresponding to right arm of a patient; stabilizing the left arm of a patient across a midsagittal plane of the patient with the left radial base; joining a radiation reduction barrier proximate the right side of the procedure table spaced apart from the left radial base, the radiation reduction barrier having a radiodense material disposed between the patient and an attending staff member; and performing a lower extremity peripheral intervention on the procedure table through the left arm of the patient from the right side of the operating table.

Additional aspects of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the disclosure without departing from the spirit and scope of the subject matter. Variations may include, but are not limited to, substitution of equivalent means, features, or steps for those illustrated, referenced, or discussed, and the functional, operational, or positional reversal of various parts, features, steps, or the like. Those of ordinary skill in the art will better appreciate the features and aspects of such variations upon review of the remainder of the specification.

BRIEF DESCRIPTION OF THE DRAWINGS

A full and enabling disclosure of the present subject matter, including the best mode thereof, directed to one of ordinary skill in the art, is set forth in the specification, which refers to the appended figures, in which:

FIG. 5 is a plan view of another feature of the system as in FIG. 1, and FIGS. 5A-5D are respective end and side views of this aspect;

FIG. 6 is an elevational view of another aspect of the system as in FIG. 1;

FIG. 7A is an elevational view of a further feature of the system as in FIG. 1 and FIG. 7B is an end view of the feature as in FIG. 7A;

FIG. 9 is an elevational view of a portion of a system according to an aspect of the disclosure;

FIG. 10 is a plan view of the system as in FIG. 9; and

FIG. 11 shows in parts 11A and 11B results of a radiation scatter survey of an embodiment according to the disclosure.

DETAILED DESCRIPTION OF THE DISCLOSURE

Figure 1:
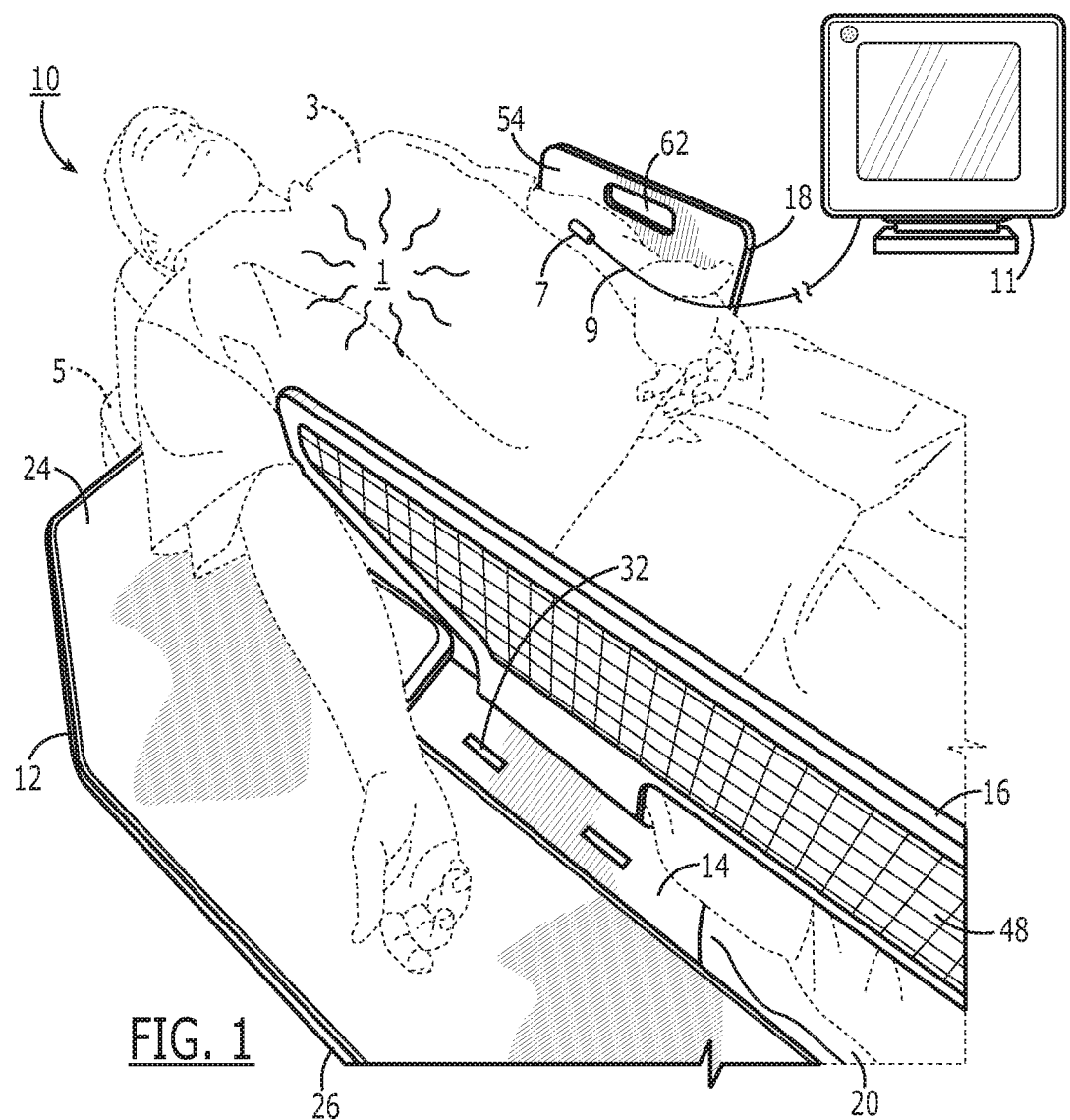
FIG. 1 is a partial perspective view of an operating system according to an aspect of the disclosure.

Detailed reference will now be made to the drawings in which examples embodying the present subject matter are shown. The detailed description uses numerical and letter designations to refer to features of the drawings.

The drawings and detailed description provide a full and written description of the present subject matter, and of the manner and process of making and using various exemplary embodiments, so as to enable one skilled in the pertinent art to make and use them, as well as the best mode of carrying out the exemplary embodiments. However, the examples set forth in the drawings and in the detailed description are provided by way of explanation only and are not meant as limitations of the disclosure. The present subject matter thus includes any modifications and variations of the following examples as come within the scope of the appended claims and their equivalents.

Turning now to FIG. 1, a trans-radial access catheter operating system is designated in general by the number 10. The system 10 is structured in general for left radial access, right room operation by permitting a doctor to remain on a right side of an operating table while simultaneously reducing radiation in inferior and superior regions relative to the operating table. The system 10 broadly includes a right radial base or deck 12, a base board, main base or platform 14, a superior radiation shield or barrier 16, which may include a unitary or insertable radiation reducing material 48, a left radial base, wall or fence 18, an inferior right radiation apron or curtain 20, and an inferior left radiation apron or curtain 22 (see FIG. 2). The exemplary components of the trans-radial access catheter operating system 10 may be made from durable, water-resistant, reusable materials that are susceptible to high pressure and/or heated sterilization and may also be constructed to block or permit passage of radiation.

In the example of FIG. 1, a cardiac or lower peripheral patient 3 is placed on a procedure or operating table 5 that hosts the main platform 14. The deck 12, the radiation shield 16, and the left radial base 18 may be in connection with the platform 14 or attached to the platform 14 via mechanical connections that may include slots or holes 36 formed in a first or top side 32 of the platform 14. As shown, a right arm of the cardiac patient 3 may be laid along a first surface or first arm side 24 opposite a second surface or connection or bottom side 26 of the right radial base 12. Also shown, a first or interior face or side 54 of the fence 18 positions a left arm of the patient 3 across a midsagittal plane or center line 70 of the patient 3 (see FIG. 2). A board or brace (not shown) may be provided to stabilize and immobilize the arm for preliminary access procedures and until the fence 18 is positioned. As will be explained in greater detail below, the fence 18 may be adjusted relative to the platform 14 and to accommodate the patient 3. A handle 62 may be provided to carry and position the left radial base 18.

As further shown in FIG. 1, one or more medical instruments 7 (shown schematically) are introduced through a sheath 9 in the stabilized left arm. X-ray or fluoroscopic imaging systems or other types of medical imaging systems are used by a doctor or staff on the right side of the table 5, also referred to as the staff side or patient right arm side, to visualize on appropriate equipment or monitor 11 the positioning of the medical instruments 7 in the patient 3.

The exemplary deck 12 in FIG. 1 is made of transradiant or radiotransparent material such as high-density polyethylene (HDPE). Thus, the deck 12 is constructed to permit passage of X-ray photons 1 during imaging of a patient, for example, to assess blockages in the patient during a procedure. As shown, the first surface 24 of the deck 12 is sufficiently large, as preferred by most doctors and staff, to accommodate surgical instruments including wires, guides, balloons and stents 7, many of which may exceed 360 centimeters (cm) in length and require the space provided by the surface 24 in order to more easily access and manipulate these instruments. Also, the X-ray or ionizing radiation 1 (shown schematically in FIG. 1) passes through the patient 3, but the ionizing radiation material 48 of the radiation shield 16 blocks or attenuates any rays 1 that are scattered by the patient's body toward staff working with the instruments 7 on the right arm side of the table 5.

Figure 2:
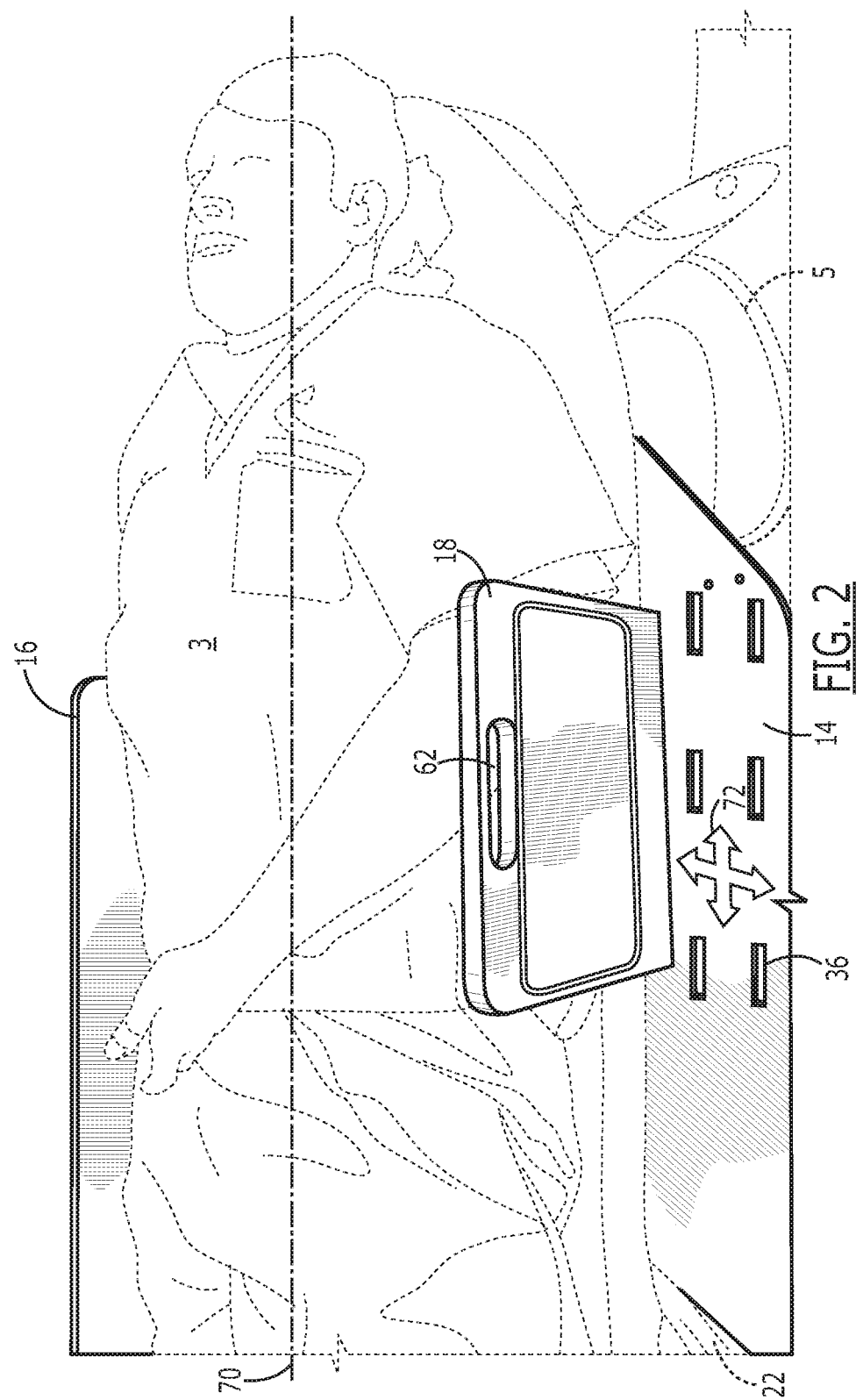
FIG. 2 is a perspective view of the system as in FIG. 1, particularly showing an exemplary feature according to an aspect of the disclosure.

FIG. 2 most clearly shows the left radial base or fence 18 located opposite the vertically disposed radiation barrier 16. As shown, the fence 18 may be releasably attached to the base board 14 via the apertures 36, which are located in this example above a portion of the radiation curtain 22 with the operating table 5 located between the body 14 and the curtain 22. As a 4-way arrow 72 indicates, the fence 18, like the radiation barrier 16, may be adjusted toward or away from the patient 3 to account for a smaller or larger patient 3 such that the left arm remains in position across the midsagittal plane 70.

Figure 3:
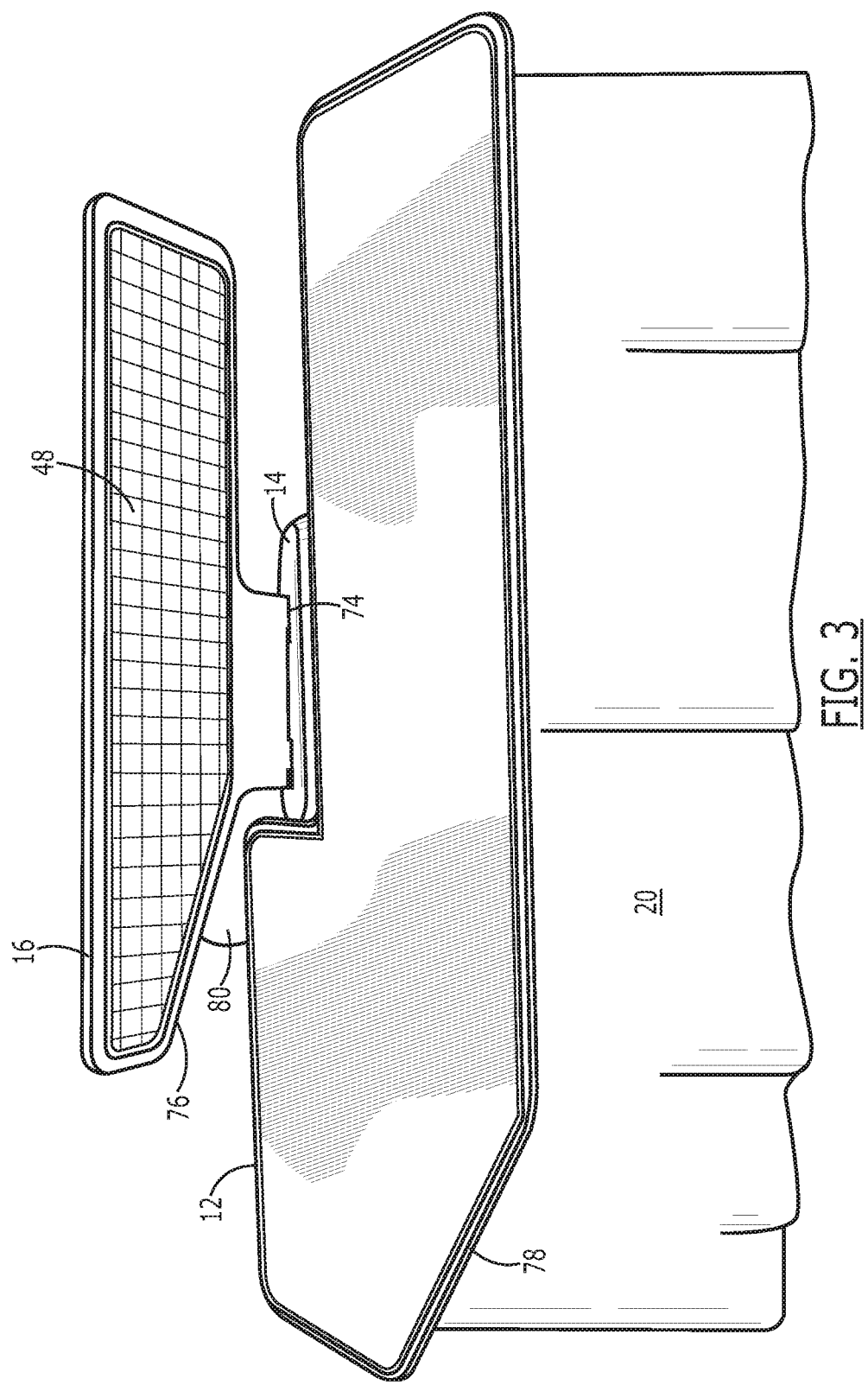
FIG. 3 is another perspective view of the system as in FIG. 1, particularly showing another exemplary feature according to an aspect of the disclosure.

FIG. 3 particularly shows a portion of the trans-radial access operating system 10 from the right side of the procedure room. As introduced, the system 10 may include the right radial base 12, the main platform 14, the radiation barrier 16, the left radial base 18, and the right radiation apron 20. Here, the radiation barrier 16 may be hollow to allow for insertion of the radiation attenuating material 48. The material 48 may be lead, antimony, tin, barium, bismuth, cesium, tungsten, or any suitable material to reduce scatter radiation. The exemplary lead 48 may be about 1/16 of an inch or about 1.58 mm in thickness and sufficiently radiodense to absorb, inhibit, attenuate, or block ionizing radiation emanating from a patient being x-rayed, i.e., scatter radiation.

FIG. 3 further shows that the right radial base 12 and the curtain 20 may be mated with the main platform 14. Alternatively, the right radial base 12 may be unitarily formed with the main platform 14. Moreover, the radiation barrier 16 may include latches, hinges, spring elements or the like 74 that permit folding of the barrier 16 down and over either the right radial base 12 or the platform 14 for patient positioning or for set-up and storage. Here, the barrier 16 may also include an angled area or cut-out 76 to permit passage of a patient's arm to the base 12 (compare, e.g., FIG. 1). An area 80 is established between the angle 76 and the base 12 that is sufficiently large for the patient's arm but not so considerable as to reduce the effective radiation reduction area of the barrier 16. The surface area 80 also provides the physician with a large, stable work surface. Also shown in this example, the base 12 is angled or has an angled area 78 to allow for a C-Arm of x-ray equipment for proper angulation. However, the deck 12 is not limited to the exemplary embodiment in FIG. 3 and may be constructed with a different surface area or geometries, including a lip at area 78 to secure surgical instruments on the deck 12.

Figure 4:
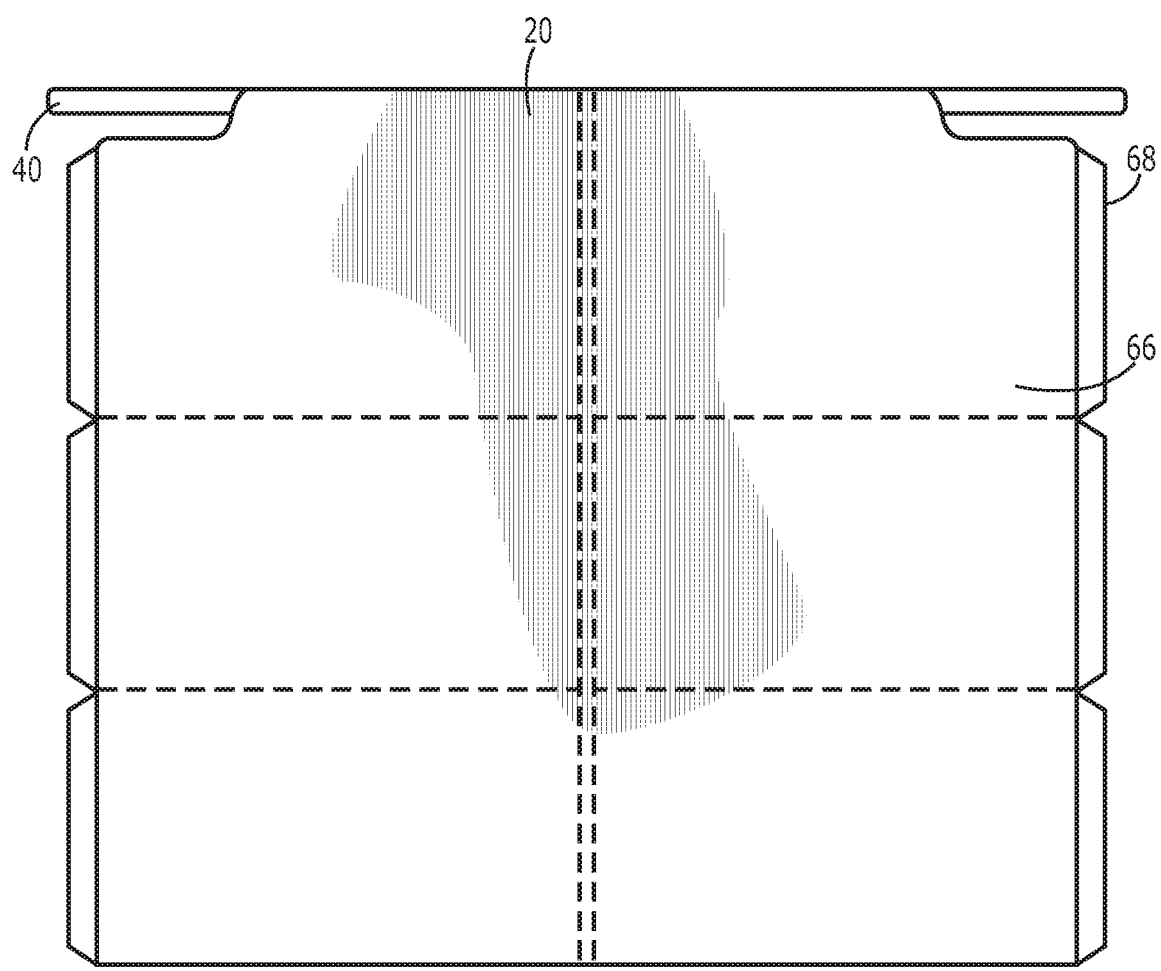
FIG. 4 is an elevational view of an aspect of the system as in FIG. 1.

With continued reference to FIG. 3 as well as FIG. 4, the right radiation apron 20 may be attachable to the platform 14 via brackets or connection devices 40. The curtain 20, similar to the radiation barrier 16, may be made of radiation absorbing or reducing material 68 such as lead, antimony, tin, barium, bismuth, cesium, tungsten, and the like. In this example, the curtain 20 includes a series of pockets or sleeves 66 into which respective material slabs or inserts 68 are placed. This arrangement may be preferred to a solitary lead (Pb) apron, for instance, in order to reduce the weight of the curtain 20 when it is being attached to the deck 12 or the platform 14; to wash the curtain 20 more easily; and/or to replace the inserts 68 with different or thicker radiodense materials as needed.

Turning now to FIG. 5 and its side and end views in FIGS. 5A-5D, the base board 14 as briefly introduced is most clearly shown. As noted, the board 14 may be unitarily constructed with the right radial base 12 but in this example, a series of slots or holes 36 in the first or top side 32 extend through the second or bottom side 34 to permit component placements tailored to accommodate different sized patients. As shown, the board 14 may include a radiation reducing layer or insert 38 on or within the board 14 that sits under the operating table (not shown) but does not interfere with patient imaging. This insert 38 may be positioned within and between radiation curtains (see, e.g., 120, 122 in FIG. 8). In one aspect, the insert 38 may be layered into the base board 14. Also shown in FIG. 5, the board 14 may include curtain or apron brackets or holders 44 that may have horizontally oriented apertures 44 or vertically oriented apertures 46 for attaching the curtains 20, 22 (see, e.g., FIGS. 1 and 2).

FIG. 6 most clearly shows the radiation barrier 16 as in FIG. 3. As noted above, the barrier 16 may be constructed entirely from radiation attenuating material 48, or the barrier 16 may be hollow for insertion of the material 48. A handle 52 may be provided for carrying the barrier 16 and for manipulating its installation and removal from the base board 14 or procedure table 5 as previously introduced. In this example, the radiation barrier 16 may include one or more connectors such as L-shaped tabs 58. These connectors 58 are inserted at an angle into the slots 36 as shown in FIG. 1 and the barrier 16 is then pressed or snapped into place substantially perpendicular to the operating table 5. The handle 52 may be used to quickly pull the barrier 16 up and out of the slots 36 to adjust the barrier 16 or for cleaning and storage.

With reference to FIGS. 7A and 7B, the left radial base 18 of the system 10 is shown most clearly. Here, the base 18 includes a first, staff, or patient side 54 and a second or outer side 56. The handle 62, briefly introduced above, is for transporting and positioning the base 18. As shown, the left radial base 18 may include one or more tabs or inserts 58 for insertion through the holes 36 of the board 14 (see, e.g., FIG. 5). In this example, the inserts 58 are L-shaped with a lower portion having a rectangular shaped extension. This construction permits insertion into the holes 36 at an angle and once in place, the base 18 is pushed down and in contact with the board 14 to lock the base 18 in place. Due to the pressure to be exerted by a patient's left arm against the base 18, a brace, block or step 64 may be included on either or both sides 54, 56 to assist with stability. Also, on the patient side 54, an arm rest, cushion, pad or padded projection 60 is provided which faces in a direction of the patient. The arm rest 60 ensures that the left arm, particularly the left wrist, crosses the midsagittal plane 70 (see, e.g., patient 3 in FIG. 2) and can also provide padding for the comfort and protection of the arm of the patient in a manner that promotes proper wrist supination to allow for safe and efficient access to the patient's right artery.

Figure 8:
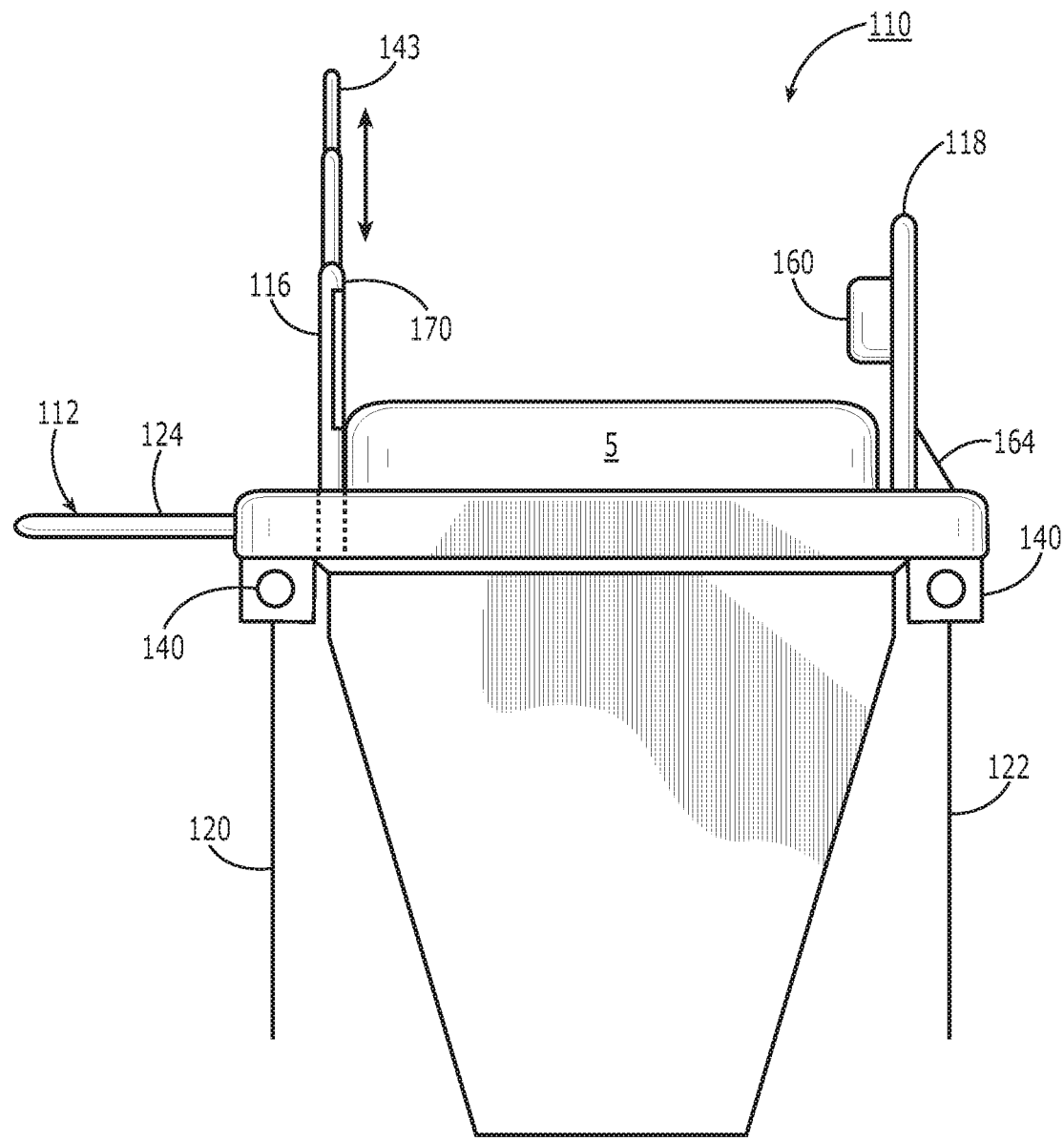
FIG. 8 is an elevational end view of an operating system according to another aspect of the disclosure.

In the embodiment shown in FIG. 8, a trans-radial access system is designated in general by the number 110. The system 110 is designed for left radial access, right room operation as it permits a doctor to remain on a right side of a procedure table while simultaneously reducing scatter radiation to the doctor emanating from inferior and superior regions relative to the table, i.e., areas respectively above and below the table 5. The system 110 generally includes a right radial base or platform 112 having an arm surface 124, a radiation shield or barrier 116, which may include a unitary or insertable radiation reducing material 148, a left radial base, wall or fence 118 with an arm cushion 160 and a stand 164, a right radiation apron or curtain 120, and a left radiation apron or curtain 122. The exemplary components of the trans-radial access system 110 may be made from durable, reusable materials that are susceptible to high pressure and/or heated sterilization and may have radiation attenuation or blocking characteristics or alternatively, may permit passage of radiation.

As FIG. 8 shows, the radiation shield 116, the left radial base 118, and the radiation aprons 120, 122 may be connected to the platform 112 via connecting devices or components 140, although other attachment means may be used in the alternative or in addition to mechanisms 140, such as snaps, snap-in ball joints, or the like. FIG. 8 also shows that the radiation shield 116 may substantially perpendicular to the platform 112 and may have a tunnel or interior compartment 170 in which a radiation insert 148 may be housed. The insert 148 may be extended away from the table 5 to increase the height or width of the insert 148 as needed, such as by telescoping or unfolding sections of the insert 148. In this example, the insert 148 is a radiation absorbing material such as lead, cadmium, rhodium, or the like. In the case of an unusually large patient, a portion of the insert 148 may be extracted from the compartment 170 and pulled up and away from the table 5 to increase a height of the radiation shield 116 to protect a doctor or staff from radiation being scattered from a patient's body during x-ray or other medical imaging.

Turning to FIG. 9, an inferior radiation shield or drape is designated by the number 220. The drape 220 may be attached to a base or main board 214 and may be divided into multiple sections such as sections 220A and 220B. Here, the two sections 220A, 220B overlap one another at area 272. More particularly, the sections 220A, 220B each have loops or other connectors or attachments 274 that are in connection with bars, rods, or other connection devices 240A, 240B. The rod 240A may be inserted or connected to a swivel assembly 276 that permits rotation of at least one of the sections 220A, 220B from about 0 to 45 degrees relative to the base board 214. For instance, the assembly 276 may include an upper portion or section 276A and a lower section 276B. The rod 240A may be inserted into the lower section 276B while the other bar 240B may be stationary or fixed and connected to upper portion 276A and to another connection point or device 278. Also shown, a drive handle 280 may be provided for a technologist to arrange the adjustable components of the system, such as by rotating section 276B relative to section 276A in order to move drape 220A.

FIG. 9 further shows that the drape sections 220A, 220B may be constructed with sections, sleeves or pockets 266 to receive insertable lead (Pb) boards 268 (shown in phantom) or other radiation attenuating or blocking materials suitable to block radiation. More specifically, the insertable boards 268 may be radiodense, radiation absorbing or reducing material such as lead, antimony, tin, barium, bismuth, cesium, tungsten, and the like and may be from about 1/16 inch to about 1/4 inch in thickness.

FIG. 10 most clearly shows the rod 240A in connection with the swivel assembly 276 to permit rotation of the rod 240A (and therefore curtain section 220A shown in FIG. 9). As shown, the rod 240A may be adjusted, swiveled or rotated from about zero degrees to about 45 degrees as depicted by angle 282 relative to the base board 214. Further shown, the bar 240B may be attached to or inserted into the assembly 276 as well as the device 278. This adjustable arrangement may provide further scatter radiation protection to staff standing in a direction nearer the device 278. The overlap provided at area 272 (see FIG. 9) will block scatter radiation with the rod 240A swiveled outward.

EXPERIMENTAL RESULTS

Introduction

On Jun. 22, 2013, a testing service conducted a radiation scatter survey in a heart catheterization room on a prototype based on the embodiments of the present disclosure; i.e., a left radial access right room setup peripheral interventional platform designed to allow a physician to perform lower extremity peripheral, heart catheterizations and pacemaker procedures while simultaneously reducing scatter radiation exposure to the cardiologist and the procedure staff such as the technologist. The purpose of the survey was to determine the percentage and effectiveness of the prototype to reduce scatter radiation levels to the cardiologist and the procedure staff Equipment and Set-Up.

The x-ray unit used for the survey was a GE Innova 2100. Cardio mode was selected on the unit with indicated techniques of 60 kvp, 4 mA, 0.5 mm Cu filtration, and a field of view (FOV) of 20 cm. Radiation scatter readings were taken using a Victoreen and Inovision digital ion chamber in the exposure rate mode, using a five second exposure time. To duplicate a patient, a phantom consisting of a square plastic container with 23 cm of water was used as the radiation scatter medium.

Measurements and Test Results.

The radiation measurements were made at the normal location [right side of operating table] for the cardiologist and the technologist with traditional radiation shielding in place and with the addition of the prototype. The radiation measurements were taken at each position at the following strategic body locations: eyes, chest, waist, and knees. Radiation measurements were also taken at five different C-arm angle positions typically used in heart catheterization procedures. As shown in detail in FIG. 11 (parts 11A and 11B), the test results indicated an overall exposure rate reduction to the technologist by 50.8% and to the cardiologist by 64.4%. More specifically, radiation reduction to the cardiologist at eye level was 39%; at chest level: 71.7%; at waist level: 76.7%; and at knee level: 70.45%. In short, radiation reduction exposure to attending staff may be reduced by between about thirty percent to about seventy-seven percent over a system that lacks the radiodense aspects described herein. Significantly reduced radiation exposure to procedure staff not only protects these professionals from unnecessary scatter radiation, but such reductions increase their procedure room longevity based on parameters mandated by federal and state radiation exposure limits.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

That which is claimed is:

1. A left radial access, right room operation peripheral intervention system for use with an imaging system, the peripheral intervention system comprising:
    a left radial fence being configured to stabilize a left arm of a patient across a midsagittal plane of the patient during a lower extremity peripheral intervention on a procedure table;
    a right radial deck disposed substantially parallel to an operating surface of the procedure table, the right radial deck being transradiant and configured to position a right arm of the patient in a direction away from the midsagittal plane during the lower extremity peripheral intervention; and
    a radiation reduction barrier disposed substantially perpendicular to the right radial deck and spaced apart from the left radial fence, the radiation reduction barrier having a radiodense material disposed between the patient and an attending staff member to reduce scatter radiation from the patient in a direction of the staff member during a procedure.

2. The left radial access, right room operation peripheral intervention system as in claim 1, wherein the left radial fence includes a support surface for contacting the left arm.

3. The left radial access, right room operation peripheral intervention system as in claim 2, further comprising a pad depending from the support surface.

4. The left radial access, right room operation peripheral intervention system as in claim 1, further comprising a base board being configured to receive the right radial deck, the left radial fence and the radiation reduction barrier.

5. The left radial access, right room operation peripheral intervention system as in claim 1, further comprising at least one radiodense apron in releasable connection proximate the operating table.

6. The left radial access, right room operation peripheral intervention system as in claim 5, wherein the radiodense apron includes a plurality of pockets and respective radiodense inserts configured for insertion in the pockets.

7. The left radial access, right room operation peripheral intervention system as in claim 5, wherein the radiodense apron and the radiation reduction barrier are disposed in a plane substantially parallel to each other.

8. The left radial access, right room operation peripheral intervention system as in claim 7, wherein scatter radiation reduction exposure to an attending physician is reduced by at least sixty percent over a system without the radiodense apron and the radiation reduction barrier.

9. The left radial access, right room operation peripheral intervention system as in claim 7, wherein scatter radiation reduction exposure to attending staff is reduced by between about thirty percent to about seventy-seven percent over a system omitting the radiodense apron and the radiation reduction barrier.

10. A left radial access, right room operation peripheral intervention system for use with an imaging system, the peripheral intervention system comprising:
    a base board being configured for connection proximate a table having a left side and a right side corresponding to a left arm and a right arm of a patient;
    a left radial fence attached to the base board and being configured to cushion and stabilize a left arm of a cardiac patient across a midsagittal plane of the patient during a lower extremity peripheral intervention on the table, wherein an attending cardiologist may perform the intervention from the right side of the table; and
    a radiation reduction barrier arranged vertically and spaced apart from the left radial fence, the radiation reduction barrier having a radiodense material disposed between the patient and an attending staff member to reduce radiation scattering from the patient in a direction of the staff member.

11. The left radial access, right room operation peripheral intervention system as in claim 10, further comprising a right radial deck disposed substantially parallel to an operating surface of the table, the right radial deck being transradiant and configured to position a right arm of the patient in a direction away from the midsagittal plane during the lower extremity peripheral intervention.

12. The left radial access, right room operation peripheral intervention system as in claim 11, wherein the right radial deck is attached to the base board.

13. The left radial access, right room operation peripheral intervention system as in claim 10, further comprising at least one radiodense apron releasably connected to the base board.

14. A left radial access, right room operation peripheral intervention system for use with an imaging system, the peripheral intervention system comprising:
    a base board being configured for attachment proximate a procedure table;
    a left radial fence attachable to the base board and being configured to stabilize a left arm of a patient across a midsagittal plane of the patient during a lower extremity peripheral intervention on the procedure table;
    a right radial deck attachable to the base board and disposed substantially parallel to an operating surface of the procedure table, the right radial deck being transradiant and configured to position a right arm of the patient in a direction away from the midsagittal plane during the lower extremity peripheral intervention;
    a radiation reduction barrier attachable to the base board and spaced apart from the left radial fence and from the right radial deck, the radiation reduction barrier having a radiodense material disposed substantially vertically between the patient and an attending staff member to reduce radiation scattering from the patient in a direction of the staff member during an imaging procedure; and
    a radiodense apron releasably connected to the base board.

15. The left radial access, right room operation peripheral intervention system as in claim 14, wherein the radiation reduction barrier includes radiation attenuating material being configured for extension.

16. The left radial access, right room operation peripheral intervention system as in claim 14, wherein the radiodense apron includes a plurality of sleeves and respective radiodense material inserts.

17. The left radial access, right room operation peripheral intervention system as in claim 14, further comprising at least two radiodense aprons.

18. A left radial access, right room operation peripheral intervention system for use with an imaging system, the peripheral intervention system comprising:
   a right radial deck having a base board attachable to a procedure table with a right side and a left side corresponding to a right arm and a left arm of a patient, the right radial deck being disposed substantially parallel to an operating surface of the operating table, the right radial deck board being disposed under the operating surface, the right radial deck being transradiant and configured to position the right arm of the patient in a direction away from the midsagittal plane during the lower extremity peripheral intervention;
   a left radial fence in connection with the base board and being configured to stabilize a left arm of a patient across a midsagittal plane of the patient during a lower extremity peripheral intervention on the procedure table;
   a radiation reduction barrier attachable to the base board under the table surface, the radiation reduction barrier spaced apart from the left radial fence and from the right radial deck, the radiation reduction barrier having a radiodense material disposed between the patient and an attending staff member to reduce radiation scattering from the patient in a direction of the staff member during an imaging procedure; and
   a radiodense apron releasably connected to the base board.

19. The left radial access, right room operation peripheral intervention system as in claim 18, wherein the radiodense apron includes at least two radiodense aprons, at least one apron movable relative to the other.

20. A method for left radial access and right room operation peripheral intervention, the method comprising:
   joining a left radial fence proximate a procedure table having a left side corresponding to a left arm of a patient and a right side corresponding to a right arm of the patient, the left radial fence being configured to stabilize the left arm of the patient during a lower extremity peripheral intervention on the procedure table;
   stabilizing the left arm of the patient across the midsagittal plane of the patient with the left radial fence;
   joining a right radial deck substantially parallel to an operating surface of the procedure table, the right radial deck being transradiant and configured to position the right arm of the patient in a direction away from the midsagittal plane during the lower extremity peripheral intervention>##
   joining a radiation reduction barrier proximate the right side of the procedure table spaced apart from the left radial fence #and disposed substantially perpendicular to the right radial deck, the radiation reduction barrier having a radiodense material disposed substantially vertically between the patient and an attending staff member to reduce scatter radiation from the patient in a direction of the staff member during a procedure; and
   performing the lower extremity peripheral intervention on the procedure table through the left arm of the patient from the right side of the procedure table.

21. The method as in claim 20, further comprising joining a base board proximate the procedure table and attaching at least one of the left radial fence and the radiation reduction barrier to the base board.

22. The method as in claim 20, further comprising joining a radiation reduction curtain proximate the procedure table.

23. The method as in claim 22, further comprising reducing radiation scattering from the patient in a direction of the staff member by at least sixty percent over a system lacking the radiation reduction barrier and the radiation reduction curtain.

* * * * *